US006929636B1

(12) United States Patent
von Alten

(10) Patent No.: US 6,929,636 B1
(45) Date of Patent: Aug. 16, 2005

(54) INTERNAL DRUG DISPENSER CAPSULE MEDICAL DEVICE

(75) Inventor: Thomas W. von Alten, Boise, ID (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 763 days.

(21) Appl. No.: 09/710,028

(22) Filed: Nov. 8, 2000

(51) Int. Cl.$^7$ ............................................. A61K 9/22
(52) U.S. Cl. ................................................. 604/890.1
(58) Field of Search .................. 604/114, 113, 65, 604/66, 67, 891.1, 892.1, 890.1, 19–21, 30–31, 604/151

(56) References Cited

U.S. PATENT DOCUMENTS

| | | | |
|---|---|---|---|
| 3,971,362 A | 7/1976 | Pope et al. ..................... 128/2 |
| 4,003,379 A * | 1/1977 | Ellinwood, Jr. .......... 604/891.1 |
| 4,146,029 A | 3/1979 | Ellinwood, Jr. ............. 128/260 |
| 4,425,117 A | 1/1984 | Hugemann et al. ........... 604/93 |
| 4,439,197 A | 3/1984 | Honda et al. ................ 604/891 |
| 4,447,224 A * | 5/1984 | DeCant et al. ................. 604/67 |
| 4,507,115 A | 3/1985 | Kambara et al. ............ 604/135 |
| 4,559,037 A * | 12/1985 | Franetzki et al. ............ 604/151 |
| 4,585,652 A | 4/1986 | Miller et al. ................... 424/83 |
| 4,793,825 A | 12/1988 | Benjamin et al. ......... 604/891.1 |
| 4,844,076 A | 7/1989 | Lesho et al. ................. 128/631 |
| 5,170,801 A | 12/1992 | Casper et al. ................ 128/769 |
| 5,217,449 A | 6/1993 | Yuda et al. ................ 604/890.1 |
| 5,279,607 A * | 1/1994 | Schentag et al. ......... 604/890.1 |
| 5,318,557 A * | 6/1994 | Gross ....................... 604/891.1 |
| 5,415,181 A | 5/1995 | Hogrefe et al. ............. 128/736 |
| 5,557,596 A | 9/1996 | Gibson et al. ............... 369/101 |
| 5,797,898 A | 8/1998 | Santini, Jr. et al. ...... 604/890.1 |
| 5,925,030 A | 7/1999 | Gross et al. .............. 604/890.1 |
| 5,984,875 A | 11/1999 | Brune ......................... 600/549 |
| 6,068,853 A | 5/2000 | Giannos et al. .............. 424/449 |
| 6,508,808 B1 * | 1/2003 | Carr et al. ................ 604/892.1 |
| 6,533,733 B1 * | 3/2003 | Ericson et al. .............. 600/561 |

FOREIGN PATENT DOCUMENTS

| | | |
|---|---|---|
| EP | 0734017 A1 | 3/1996 |
| JP | 58194809 A | 11/1983 |
| JP | 5007573 A | 7/1991 |
| WO | WO 92/21307 | 12/1992 |

OTHER PUBLICATIONS

"Laser-induced crystallization of amorphous GeTe: A time-resolved study," Physical Review B, Condensed Matter, The American Physical Society, through the American Institute of Physics, pp. 1595-1604, vol. 36, No. 3, Jul. 15, 1987.

"Novel Polysilicon Comb Actuators for XY-Stages" V. P. Jaecklin, C. Linder, N. F. de Rooij, J. M. Moret, R. Bischof and F. Rudolf, Micro Electro Mechanical Systems, An Investigation of Micro Structures, Sensors, Actuators, Machines and Robots, pp. 147-149, IEEE Proceedings 1992, IEEE Catalog No. 92CH3093-2.

"Physical Properties of Thin-Film Field Emission Cathodes With Molybdenum Cones," C. A. Spindt, I. Brodie, L. Humphrey, and E. R. Westerberg, pp. 5248-5263, Journal of Applied Physics, Dec. 1976, vol. 47, No. 12.

(Continued)

Primary Examiner—Manuel Mendez

(57) ABSTRACT

The present invention provides a swallowable internal drug medical device. The device includes a swallowable capsule. A sensing module is disposed in the capsule. A bioactive substance dispenser is disposed in the capsule. A memory and logic component is disposed in the capsule and in communication with the sensing module and the dispenser.

25 Claims, 5 Drawing Sheets

OTHER PUBLICATIONS

New York Times, May 30, 2000, "A Little Pill with a Zoom Lens".

"'Camera in a Pill' Views Digestive Tract," The New York Times, Science Desk, May 30, 2000.

Partial Search Report mailed Sep. 1, 2002.

"Silicon Field Emission Transistors and Diodes," Gary W. Jones, C. T. Sune, and Henry F. Gray, IEEE Transactions on Components, Hybrids, and Manufacturing Technology, 1051-1055, Dec. 1992, vol. 15, No. 6.

"Electron Beam-Induced Information Storage in Hydrogenated Amorphous Silicon Devices," B. G. Yacobi, pp. 695-697, Appl. Phys. Lett. 44 (7), Apr. 1, 1984.

"Silicon Micromechanics: Sensors and Actuators On A Chip," Roger T. Howe, Richard S. Muller, Kaigham J. Gabriel and William S. N. Trimmer, pp. 29-35, IEEE Spectrum, Jul. 1990.

* cited by examiner

INTERNAL DRUG DISPENSER CAPSULE MEDICAL DEVICE

CROSS REFERENCE TO RELATED APPLICATIONS

This patent application is related to Non-Provisional U.S. patent application Ser. No. 09/710,161, entitled "SWALLOWABLE DATA RECORDER CAPSULE MEDICAL DEVICE," having 09/710,161; which is filed on even date herewith, is assigned to the same assignee as the present application, and is herein incorporated by reference.

THE FIELD OF THE INVENTION

The present invention generally relates to intrabody drug dispensers, and more particularly, an ingestible drug dispenser capsule medical device.

BACKGROUND OF THE INVENTION

Dispensing a drug or other bioactive substance within a digestive tract of a body poses at least two basic issues. First, one must identify the proper location within the digestive tract for dispensing the drug from the capsule. Second, the drug must be selectively released at the identified location and/or at an appropriate point in time.

In one example, inert, ingestible medical capsules are known which are capable of sensing a single condition such as temperature or pH within the digestive tract and then transmitting that sensed temperature or sensed pH data to a receiver located remotely outside of the body. This sensed data can help identify a body location for dispensing a drug. Since the capsule is inert, i.e. non-digestible, the capsule can be reused for subsequent procedures. Use of this medical capsule requires the patient to be located closely to the remote data receiver for an extended period of time to insure that the sensed data is properly transmitted to the remote receiver. Sensor-only capsules are not capable of dispensing a drug from the capsule.

In another example, other inert, ingestible medical capsules are known which can both sense biologic data and selectively dispense drugs within the digestive tract. The capsule is ingested and initially operates much like the previously described sensor-only capsules, transmitting data such as temperature or pH to a receiver remotely located outside the body. Upon the desired sensed data being detected, a transmitter remotely located outside the body sends an activation signal to a receiver within the capsule to initiate dispensing of the drug from the capsule within the digestive tract. Additional means such as known radiographic techniques can be used to further identify the location of the capsule in relation to the sensed data. Accordingly, these conventional drug dispenser capsules require the patient to be close to a transmitter/receiver remotely located outside of the body to perform the transmitting and receiving functions associated with the capsule.

Accordingly, conventional intrabody drug dispensers have several limitations. First, conventional drug dispensing capsules require a transmitter for transmitting sensed data while in the digestive tract and must be used with a remote receiver for receiving the transmitted data. Conventional drug dispenser capsules also require a receiver for receiving a drug-dispensing activation signal and must be used with a remote transmitter for transmitting the activation signal to the receiver within the capsule. In some case, these requirements force the patient to remain relatively stationary for a protracted period of time during the procedure to insure adequate proximity to the remote transmitter/receiver. The remote transmitter and/or receiver also must be used in association with a human event manager and/or a computer-driven management system to determine what signals are received and what signals should be sent, as well as when to do so. This active human management or computer-driven management raises the cost of the sensing or dispensing procedure and again requires the patient to be located adjacent the computer equipment or a human for an extended period of time. Finally, the mandatory constraint of placing a transmitter and/or receiver within the capsule makes the capsule bulkier, requires a larger capsule, or less space is available to accommodate other functional modules such as drug storage, sensors, etc.

SUMMARY OF THE INVENTION

The present invention provides a swallowable internal drug dispenser medical device. The device includes a swallowable capsule. A sensing module is disposed in the capsule. A bioactive substance dispenser is disposed in the capsule. A memory and logic component is disposed in the capsule and in communication with the sensor and the dispenser.

In one exemplary embodiment, the inert, swallowable drug dispenser capsule internally senses and internally dispenses drugs within the digestive tract of the human body. The drug dispenser capsule senses biologic information within the digestive tract with one or more type of sensors (e.g. chemical, electrical, etc.). In response to that sensed information, the capsule dispenses a bioactive substance within the digestive tract without the need to transmit or receive signals from a remote transmitter/receiver, and without active human or computer management. A memory module in the capsule includes a stored profile of biologic conditions within the digestive tract. The sensed data is evaluated relative to the profile and/or relative to predetermined criteria stored in memory. Upon the sensed data matching a particular item in the profile or meeting the predetermined criteria, the capsule dispenses the drug or other bioactive substance. In one aspect, the memory module includes an atomic resolution storage device.

DESCRIPTION OF THE PREFERRED EMBODIMENTS

Figure 1:
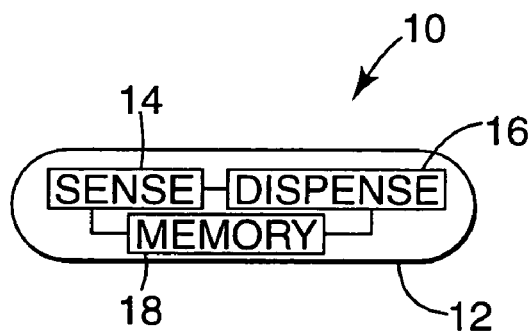
FIG. 1 is a schematic illustration of an internal drug dispenser capsule medical device, according to an embodiment of the present invention.

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

A drug dispenser capsule of the present invention internally senses a biologic condition and internally dispenses drugs within the digestive tract of a body (e.g., a human body or animal body) based upon the sensed biologic condition. The capsule is inert and is therefore swallowable and passable through the digestive tract without being consumed. The swallowable drug dispenser capsule senses information about the digestive tract or senses conditions within the digestive tract that are indicative of conditions in other organs (e.g., skin). The capsule contains one or more type of sensors (e.g. chemical, electrical, etc.) so that one or more types of biologic data can be tracked through the digestive system. In response to that sensed information, the capsule dispenses a bioactive substance within the digestive tract without the need to transmit or receive signals from a remote transmitter/receiver, and without active human or computer management.

A memory module, and more preferably, an atomic resolution storage device, in the capsule includes a stored profile of biologic conditions within the digestive tract. The data profile typically is created from a sensor-type capsule previously passed through the digestive tract. The sensed biologic data is evaluated relative to the profile and/or relative to predetermined criteria stored in memory. Upon the sensed data matching a particular item in the profile or meeting the predetermined criteria, the capsule dispenses the drug or other bioactive substance. The "on-board" evaluation of sensed data and "on-board" triggering of drug release using the memory feature of the capsule eliminates the need for simultaneous use of a closely-located remote data receiver to receive sensed data from the capsule and/or a closely-located remote signal transmitter to send drug-releasing activation signals to the capsule. Accordingly, the patient is free to move during the procedure and no active human or computer management is necessary during the procedure.

Significantly, direct interaction between the sensor and dispenser within the capsule, with the aid of memory, permits sophisticated dispensing regimens. For example, dispensing can be slowed, accelerated, stopped or started, as many times as desired, all in response to the sensed data and/or matching of sensed data with a stored profile of data and criteria. This dynamic model allows dispensing based on several types of sensed conditions, as well as changing conditions within the digestive tract. A dynamic dispensing module, which uses reclosable ports to dispense the drugs, facilitates these functions.

All of the biologic information sensed within the digestive tract can be recorded immediately in memory within the capsule for developing future profiles. In a more complex example, all data sensed throughout the digestive tract is recorded immediately to create a profile of sensed data for evaluation against predetermined criteria to determine whether or when to dispense a drug from the capsule. Moreover, this sensed data can be studied later outside of the digestive tract. Finally, while not required, the capsule optionally includes a transmitter and/or receiver for sending data to a remote location and/or for receiving commands to dispense a drug. This transmission/reception feature can be used in concert with the memory feature or alongside the memory feature of the capsule.

The atomic resolution storage device memory used in the swallowable data recorder capsule medical device according to the present invention is subminiature in size, allowing it to be contained within a swallowable capsule, has low power requirements, and provides for non-volatile storage of large amounts of data, including video. The term "atomic resolution storage device" memory as used herein is defined as a non-volatile memory storage device capable of storing a large volume of data, such as megabytes to gigabytes of data points, within a relatively small storage area and requiring very low power consumption. The atomic resolution storage device includes a field emitter, a storage medium, and a micromover and associated circuitry for the reading and writing of data. Preferably, the atomic resolution storage device includes a plurality of spaced apart field emitters, wherein each field emitter is responsible for a number of storage areas on the storage medium.

As shown generally in FIG. 1, a swallowable, internal drug dispenser capsule medical device 10 (hereafter referred to as "capsule 10") of the present invention defines shell 12 containing sensing module 14, dispensing module 16, and memory component 18. In response to sensed conditions within a digestive tract, capsule 10 dispenses a bioactive substance within the digestive tract without wireless communication to an external component outside of the body. In particular, capsule 10 is readily ingestible within a digestive tract of a human body and is inert (i.e. non-digestible) so that capsule 10 passes through the digestive tract without being consumed. Sensing module 14 senses a predetermined biologic condition within the human body such as temperature, pH, biological/chemical constituents, and/or visually recognizable landmarks internally within the human body, etc. Dispensing module 16 holds a drug and selectively dispenses the drug from capsule 10 into the digestive tract. Memory component 18 holds a stored profile of biologic data and/or predetermined criteria for evaluating the data sensed by module 14. Memory component 18 also can store data sensed by sensing module 14 for later retrieval upon capture of capsule 10 outside of the human body.

In use, capsule 10 is ingested and senses a predetermined biologic condition within the digestive tract using sensing module 14. Using memory component 18, the sensed data is evaluated relative to a profile of biologic data and/or predetermined criteria. Based upon that evaluation, dispensing module 16 is selectively activated to release a bioactive substance within the digestive tract. Significantly, evaluation of the sensed data and initiation of drug dispensing both take place "on-board" within the capsule while in the digestive tract. These internal functions occur without resort to externally stored data profiles and/or externally generated activation signals that are conventionally controlled by a remote human or computer event manager via wireless communication.

Figure 2:
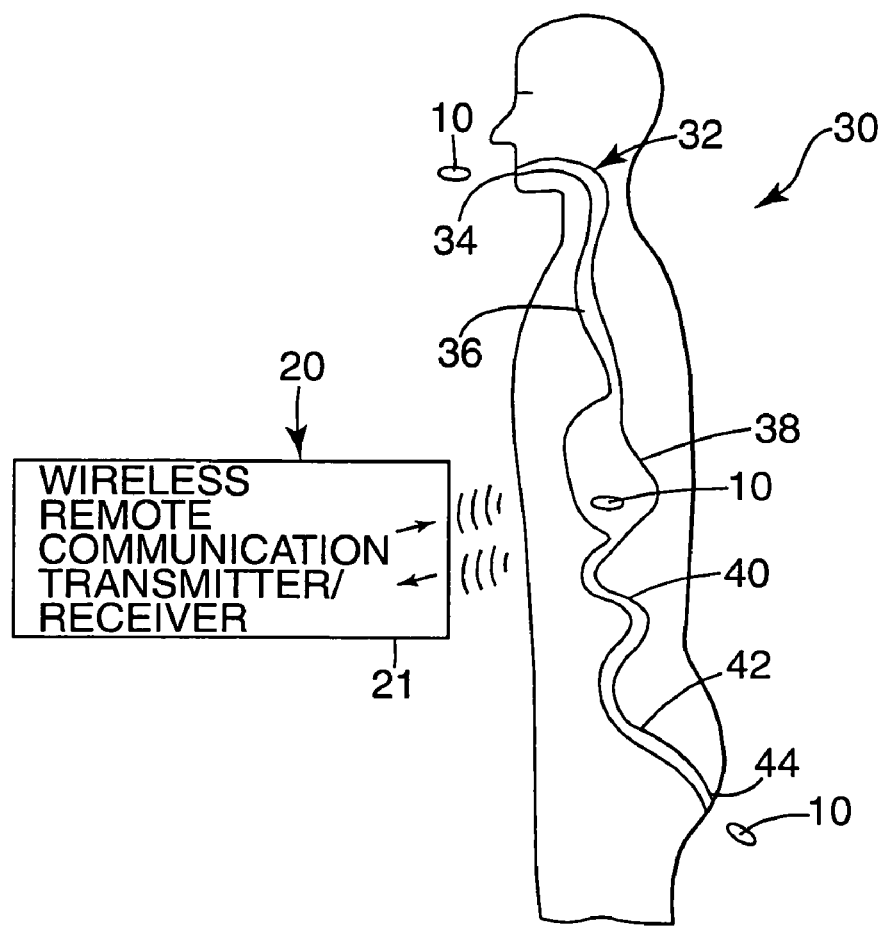
FIG. 2 is a diagram view of a digestive tract of a human body schematically showing the travel path of an internal drug dispenser capsule medical device, according to an embodiment of the present invention.

FIG. 2 shows capsule 10 in association with human body 30 including digestive tract 32 having mouth 34, esophagus 36, stomach 38, small intestine 40, large intestine 42, and rectum 44. Once ingested within mouth 34, inert capsule 10 travels the full path of digestive tract 32 until capsule 10 is captured upon exiting at rectum 44. Each of the named locations within the human body represents examples of locations at which capsule 10 can sense and record data regarding biologic conditions. Of course, operation of capsule 10 is not limited to use in the named locations as the sensing, recording, and dispensing functions of capsule 10 can be performed anywhere within digestive tract 32.

Capsule 10, particularly its shell, preferably is made of (or coated with) one or more of the following inert materials: Teflon; glass; ceramic; and other materials known to those skilled in the art. Capsule 10 preferably has a size as large as the digestive tract will allow, such as five millimeters in diameter, and preferably has a generally rounded, oblong shape, as shown in FIGS. 1–2. However, capsule 10 can take other sizes (e.g., a smaller capsule) and shapes, provided that the shapes are readily passable through digestive tract 34 and can adequately house the required sensing, dispensing, and memory modules 14,16,18.

While capsule 10 performs all of its functions entirely within digestive tract 34 without remote human or computer management, each of the sensing, recording, and dispensing functions optionally also can be activated and controlled remotely, using known wireless communication techniques (e.g. ultrasonic, radiofrequency, etc.). Accordingly, as shown in FIG. 2, capsule 10 optionally comprises a larger system including wireless communication system 20 that includes a transmitter/receiver 21 that operates with a transmitter/receiver (not shown) incorporated in capsule 10. Using these wireless communication techniques, each of the sensing, recording, and dispensing functions optionally can be initiated at a predetermined point in time or at a predetermined location.

Figure 3:
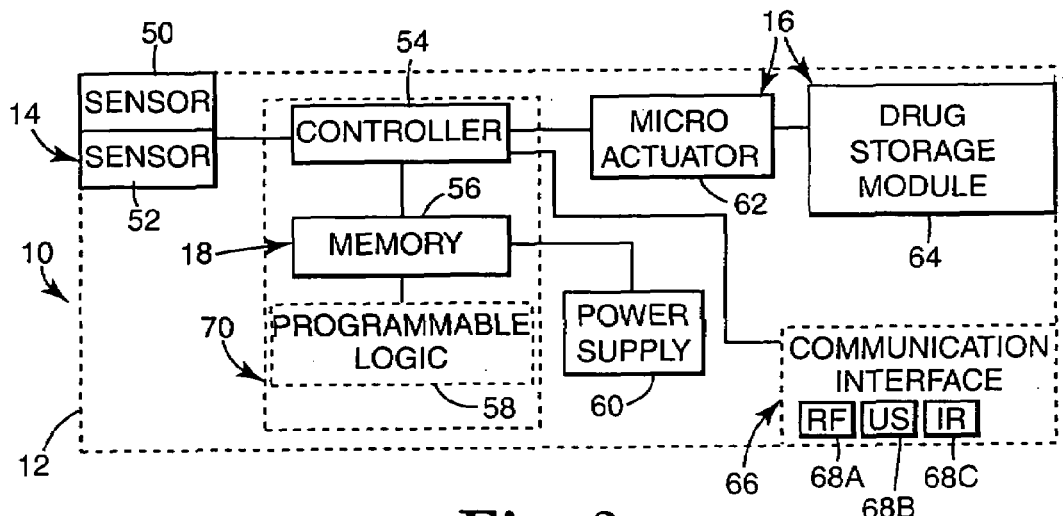
FIG. 3 is a schematic block diagram of an internal drug dispenser capsule medical device, according to an embodiment of the present invention.

FIG. 3 is a schematic diagram of swallowable drug dispensing capsule 10, illustrating capsule 10 in greater detail. As shown in FIG. 3, capsule 10 includes sensors 50, 52, controller 54, memory 56, optional programmable logic 58, power supply 60, microactuator 62, drug storage module 64, and communication interface 66 having at least one of the following types of communication modules: radiofrequency 68A; ultrasonic 68B; and/or infrared 68C. Finally, in one preferred embodiment, at least memory 56, and preferably also controller 54 and/or programmable logic 58 are embodied on a silicon-based module 70 in one or more semiconductor chips.

Sensors 50,52 further define sensing module 14 of FIG. 1. Sensors 50,52 define multiple sensors that are arranged about an outer surface of capsule 10 in a desired predetermined orientation that is expected to expose each sensor to a targeted bodily condition or landmark within the human body. Each sensor can comprise a single type of sensor such as an image detector or a different type of sensor (e.g. chemical, electrical, temperature, etc.). Chemical detectors detect the presence of many substances, such as the concentration of glucose, which is relevant to treatment of diabetes patients.

Controller 54 regulates communication between sensors 50,52 and memory 56, communication between memory 56 and any remote controllers outside of the human body, and communication with programmable logic component(s) 58. Finally, controller 54 operably controls both communication interface 66 and microactuator 62. Controller 54 preferably is a logic controller and includes a microprocessor. Controller 54 may also comprise one or more logical devices (e.g., a logic gate) capable of performing a sequence of logical operations.

Memory or storage device 56 is preferably an ultra-high capacity storage device, and which is more preferably of a silicon-based construction. In one preferred embodiment, memory 56 is an atomic resolution storage device capable of storing a large volume of data, such as megabytes to gigabytes of data points, within a relatively small storage area. The atomic resolution storage device is a low power consumption storage device, and may require less than 500 mW to operate. In one preferred embodiment, ARS module 70 has a size of about 1 square millimeter, suitable to be carried within a swallowable medical capsule. In addition, ARS module can include its own modules that correspond to the functions of programmable logic 58 and/or controller 54. Finally, other subminiature memory devices, known to those skilled in the art, that have a high storage capacity with relatively low power consumption can be used in place of ARS module. However, these alternative devices may limit the volume and quality of data recorded since these devices will not be as powerful as ARS module 70 relative to the power consumption requirements and amount of memory storage.

One atomic resolution storage device suitable for use in the swallowable data recorder capsule medical device according to the present invention is disclosed in U.S. Pat. No. 5,557,596 to Gibson et al., issued Sep. 17, 1996, entitled "Ultra-High Density Storage Device," which is incorporated herein by reference. Other suitable ultra-high density storage devices suitable for use as memory 56 with the swallowable data recorder capsule medical device according to the present invention will become apparent to those skilled in the art after reading the present application. One exemplary embodiment of a suitable ultra-high density storage device (i.e., atomic resolution storage device) suitable for use as memory 56 with the swallowable data recorder capsule medical device according to the present invention is disclosed in detail later in this application.

Drug storage module 64 and microactuator 62 further define drug dispensing module 16 of FIG. 1. Drug storage module 64 represents a container for holding a drug or bioactive substance that will be released into digestive tract 34. Accordingly, drug storage module 64 also includes one or more selectively activated dispensing ports that open in an outer surface of capsule 10. Microactuator 62 preferably is a chemically activated or electromechanically activated mechanism for causing drug storage module 64 to release its contents into the digestive tract.

A suitable power supply 60 includes a lithium-ion battery, which is relatively non-toxic. Alternatively, power supply 60 comprises a disposable, chemically-based battery, which ideally is an encapsulated removable module that can be replaced as needed. Other power supplies known to those skilled in the art that is suitable for in vivo environments can be used.

Communication interface 66 includes any suitable wireless transmission technology (e.g. ultrasonic, radiofrequency, etc.) that readily permits communication to and from capsule 10 while capsule is in digestive tract 34 and remote transmitter/receiver 21 (FIG. 1) is located remotely outside of the body. However, infrared port 68C is preferably used for communicating with capsule 10 after capsule 10 is captured from the body. Likewise, infrared port 68C preferably is used for programming controller 54, memory 56, and/or logic component 58 prior to insertion of capsule 10 within the body to determine the manner in which sensors 50,52 will operate and communicate with memory 56, as well as the manner in which microactuator 62 will operate and communicate with memory via controller 54.

In use, sensors 50,52 of capsule 10 sense biologic data within digestive tract 34 and the sensed data is passed through controller 54 for storage in memory 56 and/or comparison with a stored data profile in memory 56 and/or logic 58. After the predetermined criteria are met, controller 54 activates microactuator 62 to dispense the drug from drug storage module 64 into digestive tract 34. The sensed data optionally is stored in memory 56 and retrieved via communication interface 66 after capture of capsule 10 upon exiting digestive tract 34. Finally, wireless communication system 20 optionally is used in addition to, or as an alternative to, controller 54 and memory 56 to facilitate evaluating and storing sensed data and to dispense drugs upon selective activation at the appropriate time.

FIGS. 4 through 7 disclose one exemplary embodiment of an atomic resolution storage device capable of storing megabytes to gigabytes of information in a small storage area. For a further discussion of an atomic resolution storage device, see U.S. Pat. No. 5,557,596, entitled, "Ultra-High Density Storage Device", by Gibson et al. and assigned to Hewlett-Packard Company, which was previously incorporated herein by reference.

Figure 4:
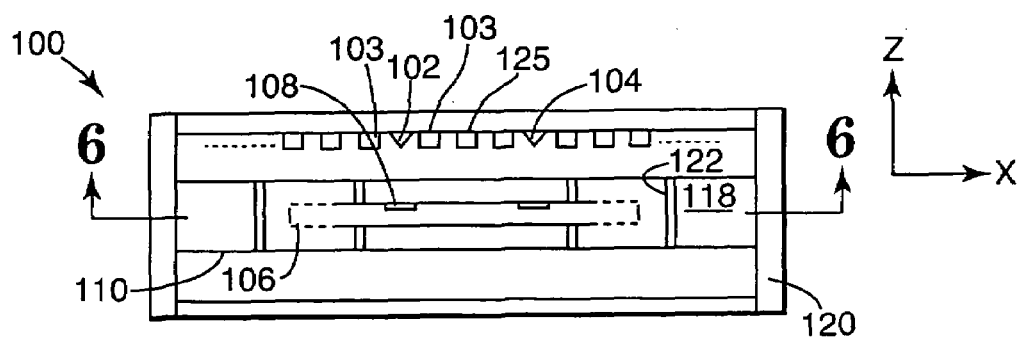
FIG. 4 is a side view illustrating one exemplary embodiment of a storage device used in an internal drug dispenser capsule medical device in accordance with the present invention.

FIG. 4 illustrates a side cross-sectional view of storage device 100. Storage device 100 is one exemplary embodiment of storage device recorder 54 including memory 56. Storage device 100 includes a number of field emitters, such as field emitters 102 and 104, storage medium 106 including a number of storage areas, such as storage area 108, and micromover 110. Micromover 110 scans storage medium 106 with respect to the field emitters or vice versa. In one preferred embodiment, each storage area is responsible for storing one bit of information.

In one embodiment, the field emitters are point emitters having relatively very sharp points. Each point emitter may have a radius of curvature in the range of approximately 1 nanometer to hundreds of nanometers. During operation, a pre-selected potential difference is applied between a field emitter and its corresponding gate, such as between field emitter 102 and gate 103 surrounding it. Due to the sharp point of the emitter, an electron beam current is extracted from the emitter towards the storage area. Depending on the distance between the emitters and the storage medium 106, the type of emitters, and the spot size (bit size) required, electron optics may be utilized to focus the electron beams. A voltage may also be applied to the storage medium 106 to either accelerate or decelerate the field-emitted electrons or to aid in focusing the field-emitted electrons.

In one embodiment, casing 120 maintains storage medium 106 in a partial vacuum, such as at least $10^{-5}$ torr. It is known in the art to fabricate such types of microfabricated field emitters in vacuum cavities using semiconductor processing techniques. See, for example, "Silicon Field Emission Transistors and Diodes," by Jones, published in IEEE Transactions on Components, Hybrids and Manufacturing Technology, 15, page 1051, 1992.

In the embodiment shown in FIG. 4, each field emitter has a corresponding storage area. In another embodiment, each field emitter is responsible for a number of storage areas. As micromover 110 scans storage medium 106 to different locations, each emitter is positioned above different storage areas. With micromover 110, an array of field emitters can scan over storage medium 106.

As will be described, the field emitters are responsible to read and write information on the storage areas by means of the electron beams they produce. Thus, field emitters suitable for use in storage device 100 are the type that can produce electron beams that are narrow enough to achieve the desired bit density on the storage medium, and can provide the power density of the beam current needed for reading from and writing to the medium. A variety of ways are known in the art that are suitable to make such field emitters. For example, one method is disclosed in "Physical Properties of Thin-Film Field Emission Cathodes With Molybdenum Cones," by Spindt et al, published in the Journal of Applied Physics, Vol. 47, No. 12, December 1976. Another method is disclosed in "Fabrication and Characteristics of Si Field Emitter Arrays," by Betsui, published in Tech. Digest $4^{th}$ Int. Vacuum Microelectronics Conf., Nagahama, Japan, page 26, 1991.

In one embodiment, there can be a two-dimensional array of emitters, such as 100 by 100 emitters, with an emitter pitch of 50 micrometers in both the X and the Y directions. Each emitter may access bits in tens of thousands to hundreds of millions of storage areas. For example, the emitters scan over the storage areas with a periodicity of about 1 to 100 nanometers between any two storage areas. Also, all of the emitters may be addressed simultaneously or in a multiplexed manner. Such a parallel accessing scheme significantly reduces access time, and increases data rate of the storage device.

Figure 5:
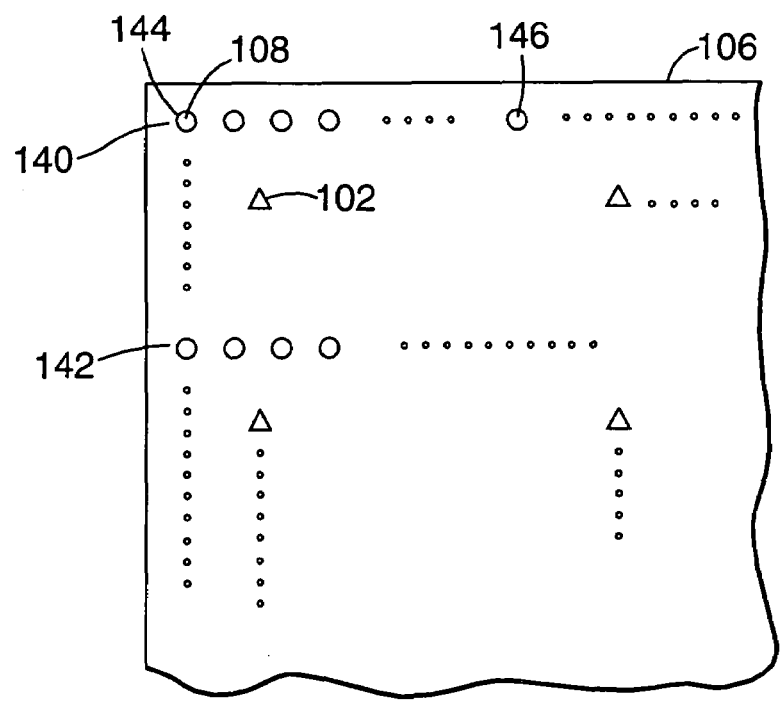
FIG. 5 is a simplified schematic diagram illustrating one exemplary embodiment of storing information within the storage device illustrated in FIG. 4.

FIG. 5 shows the top view of storage medium 100 having a two-dimensional array of storage areas and a two-dimensional array of emitters. Addressing the storage areas requires external circuits. One embodiment to reduce the number of external circuits is to separate the storage medium into rows, such as rows 140 and 142, where each row contains a number of storage areas. Each emitter is responsible for a number of rows. However, in this embodiment, each emitter is not responsible for the entire length of the rows. For example, emitter 102 is responsible for the storage areas within rows 140 through 142, and within columns 144 through 146. All rows of storage areas accessed by one emitter are connected to one external circuit. To address a storage area, one activates the emitter responsible for that storage area and moves that emitter by micromover 110 (shown in FIG. 4) to that storage area. The external circuit connected to the rows of storage areas within which that storage area lies is activated.

Micromover 110 can also be made in a variety of ways, as long as it has sufficient range and resolution to position the field emitters over the storage areas. As a conceptual example, micromover 110 is fabricated by standard semiconductor microfabrication process to scan storage medium 106 in the X and Y directions with respect to casing 120.

Figure 6:
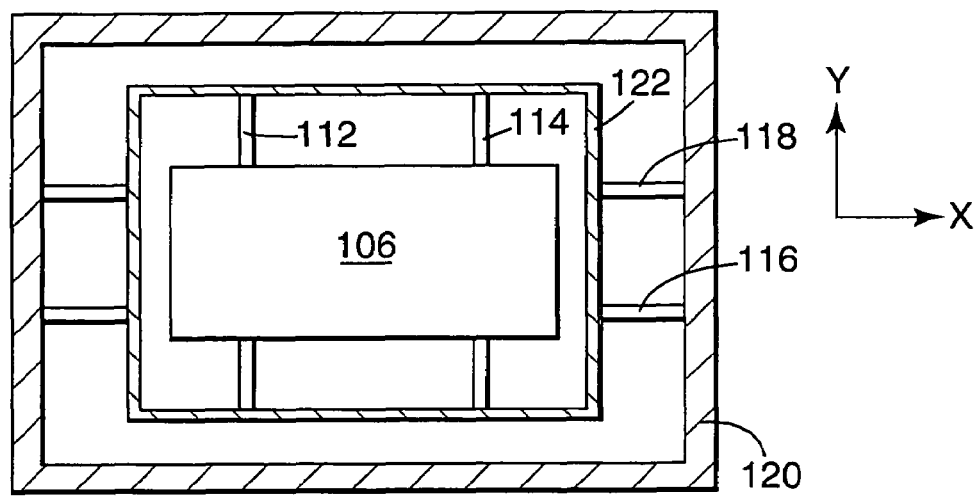
FIG. 6 is a top view illustrating one exemplary embodiment of a storage device used in an internal drug dispenser capsule medical device in accordance with the present invention taken along lines 6—6 of FIG. 4.

FIG. 6 shows the top view of the cross section 6—6 in FIG. 4, illustrating storage medium 106 held by two sets of thin-walled microfabricated beams. The faces of the first set of thin-walled beams are in the Y-Z plane, such as 112 and 114. Thin-walled beams 112 and 114 may be flexed in the X direction allowing storage medium 106 to move in the X direction with respect to casing 120. The faces of the second set of thin-walled beams are in the X–Z plane, such as 116 and 118. Thin-walled beams 116 and 118 allow storage medium 106 to move in the Y direction with respect to casing 120. Storage medium 106 is held by the first set of beams, which are connected to frame 122. Frame 122 is held by the second set of beams, which are connected to casing 120. The field emitters scan over storage medium 106, or storage medium 106 scans over the field emitters in the X–Y directions by electrostatic, electromagnetic, piezoelectric, or other means known in the art. In this example, micromover 110 moves storage medium 106 relative to the field emitters. A general discussion of such microfabricated micromover can be found, for example, in "Novel Polysilicon Comb Actuators for XY-Stages," published in the Proceeding of MicroElectro Mechanical Systems 1992, written by Jaecklin et al.; and in "Silicon Micromechanics: Sensors and Actuators on a Chip", by Howe et al., published in IEEE Spectrum, page 29, in July 1990.

In another embodiment, the electron beam currents are rastered over the surface of storage medium 106 by either electrostatically or electromagnetically deflecting them, such as by electrostatic deflectors or electrodes 125 (shown in FIG. 3A) positioned adjacent to emitter 104. Many different approaches to deflect electron beams can be found in literature on Scanning Electron Microscopy and will not be further described in this specification.

In one method, writing is accomplished by temporarily increasing the power density of the electron beam current to modify the surface state of the storage area. Reading is accomplished by observing the effect of the storage area on the electron beams, or the effect of the electron beams on the storage area. For example, a storage area that has been modified can represent a bit 1, and a storage area that has not been modified can represent a bit 0, and vice versa. In fact, the storage area can be modified to different degrees to represent more than two bits. Some modifications may be permanent, and some modifications may be reversible. The permanently modified storage medium is suitable for write-once-read-many memory (WORM).

In one embodiment, the basic idea is to alter the structure of the storage area in such a way as to vary its secondary electron emission coefficient (SEEC), its back-scattered electron coefficient (BEC), or the collection efficiency for secondary or back-scattered electrons emanating from the storage area. The SEEC is defined as the number of secondary electrons generated from the medium for each electron incident onto the surface of the medium. The BEC is defined as the fraction of the incident electrons that are scattered back from the medium. The collection efficiency for secondary/back-scattered electrons is the fraction of the secondary/back-scattered electrons that is collected by an electron collector, typically registered in the form of a current.

Reading is typically accomplished by collecting the secondary and/or back-scattered electrons when an electron beam with a lower power density is applied to storage medium 106. During reading, the power density of the electron beam should be kept low enough so that no further writing occurs.

One embodiment of storage medium 106 includes a material whose structural state can be changed from crystalline to amorphous by electron beams. The amorphous state has a different SEEC and BEC than the crystalline state, which leads to a different number of secondary and back-scattered electrons emitted from the storage area. By measuring the number of secondary and back-scattered electrons, one can determine the stage of the storage area. To change from the amorphous to crystalline state, one increases the beam power density and then slowly decreases it. This heats up the amorphous and then slowly cools it so that the area has time to anneal into its crystalline state. To change from crystalline to amorphous state, one increases the beam power density to a high level and then rapidly decreases the beam power. To read from the storage medium, a lower-energy beam strikes the storage area. An example of such type of material is germanium telluride (GeTe) and ternary alloys based on GeTe. Similar methods to modify states using laser beams as the heating source have been described in "Laser-induced Crystallization of Amorphous GeTe: A Time-Resolved Study," by Huber and Marinero, published in Physics Review B 36, page 1595, in 1987, and will not be further described here.

There are many preferred ways to induce a state change in storage medium 106. For example, a change in the topography of the medium, such as a hole or bump, will modify the SEEC and BEC of the storage medium. This modification occurs because the coefficients typically depend on the incident angle of the electron beam onto the storage area. Changes in material properties, band structure, and crystallography may also affect the coefficients. Also, the BEC depends on an atomic number, Z. Thus, one preferred storage medium has a layer of low Z material on top of a layer of high Z material or vice versa, with writing accomplished through ablating some of the top layer by an electron beam.

Figure 7:
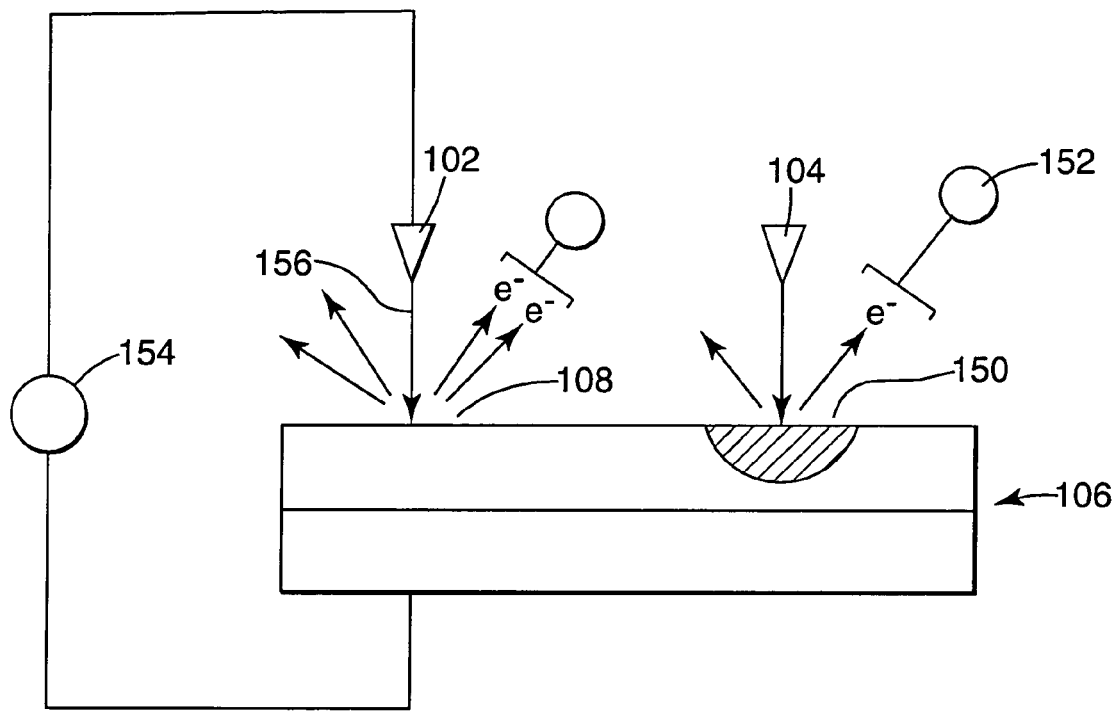
FIG. 7 is a diagram illustrating one exemplary embodiment of field emitters reading from storage areas of the storage device of FIG. 4.

FIG. 7 shows schematically the field emitters reading from storage medium 106. The state of storage area 150 has been altered, while the state of storage area 108 has not been altered. When electrons bombard a storage area, both secondary electrons and back-scattered electrons will be collected by the electron collectors, such as electron collector 152. An area that has been modified will produce a different number of secondary electrons and back-scattered electrons, as compared to an area that has not been modified. The difference may be more or may be less depending on the type of material and the type of modification. By monitoring the magnitude of the signal current collected by electron collectors 152, one can identify the state of and, in turn, the bit stored in, the storage area.

Field emitters may be noisy with the magnitude of the electron beam current varying with respect to time. Moreover, the gap distance between the tips of the emitters and the surface of the storage medium may vary. If the information stored were based on tunneling current, then the gap distance may be extremely crucial. However, the application presently disclosed depends on field emitters, and not directly on the emitted electron beam current, but rather on the effect of the beam. At least two ways may be used to alleviate the problem of the emitters being noisy. One way is to connect constant current source 154 to field emitter 102. This source will control the power density of electron beam current beam 156. Although this method would not help storage techniques using the magnitude of the field emitted current as the signal, this method reduces the field emitter noise significantly. Another way to alleviate the field-emitter noise is to separately measure the emitted electron beam current and use it to normalize the signal current. As the electron beam current varies, the signal current varies correspondingly. On the other hand, the normalized signal current remains the same to indicate the state of the storage area.

Figure 8:
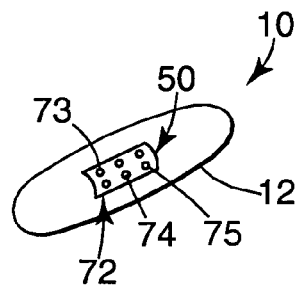
FIG. 8 is a perspective view of an internal drug dispenser capsule medical device incorporating a surface sensor array, according to an embodiment of the present invention.
Figure 9:
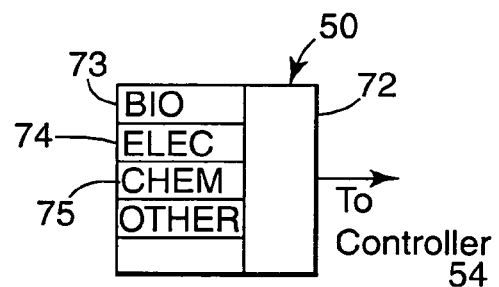
FIG. 9 is a schematic illustration of the sensor array of FIG. 8.

FIG. 8 is a perspective view of capsule 10, in which sensor module 72 further defines sensor 50 and includes sensors 73, 74, 75. Each sensor 73–75 represents the same type of sensor, or each sensor can comprise a different type of sensor. For example, as shown in FIG. 9, sensor 73 comprises a biologic condition sensor (e.g. pH), sensor 74 comprises an electrical sensor (e.g. temperature), and sensor 75 comprises a chemical sensor (e.g. sodium and/or potassium).

Sensing module 72 preferably is a silicon-based module, which includes various cavities filled with the desired type of sensing substance and/or circuitry to form each sensor 73,74,75. For example, sensor 72 preferably is constructed from a silicon surface bearing a chemically sensitized film for each sensor 73, 74, 75, wherein the film reacts upon the presence of a particular biologic constituent, producing an electrical response in the silicon surface that is recorded in memory as sensed data. In one aspect, sensing module 72 can be similar to sensing modules available from Agilent Technologies (e.g., an Agilent 2100 bioanalyzer).

For example, using these techniques sensor 72 can be selected to sense absolute values of pH, or sense pH only below or only above a certain value, e.g.

5. Sensor 72 also could be selected to sense any pH value to provide continuously variable data on pH. Alternatively, sensor 72 could sense the presence of any expected digestive tract constituent such as bile fluids, or any unexpected digestive tract constituent such as blood, or cancer cells. For example, one of the sensors 73,74,75 could be chemically sensitive to cancer cells, thus triggering release of the drug from drug storage module 64. In addition, or alternatively, this sensed data triggers ultrasonic transmission of the identified cancer constituent to a remote receiver. With this information, the location is determined based on the character of the sensed data. Alternatively, radiographic or wireless communication techniques can be used to identify the location of capsule 10 to target future diagnostic and/or therapeutic techniques at that location. This type of sensor array 72 conveniently permits a large number of the same type or different type of sensors to be placed on small electrically communicable module. This arrangement is preferred where many different types of tests must be performed.

Figure 10:
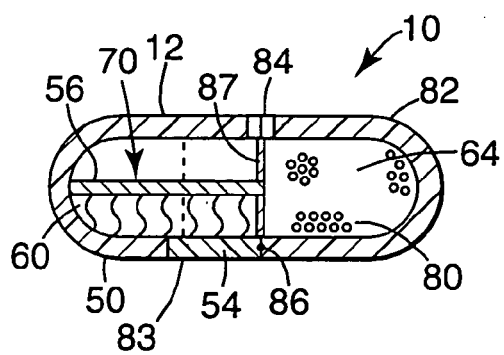
FIG. 10 is a sectional view of an internal drug dispenser capsule prior to dispensing a drug, according to an embodiment of the present invention.

FIG. 10 is a sectional view of a drug dispenser capsule 10, according to an embodiment of the present invention. As shown in FIG. 10, capsule 10 has a generally rounded oblong shape. FIG. 10 shows sensor 50, controller 54, memory 56, power supply 60, module 70, each of which have the features, attributes, and functions described in association with FIG. 3. Module 70 carries one or more semiconductor chips to provide memory 56 (and other functions) and extends through an interior of capsule 10 along a partial length of capsule 10. Sensor 50 is shown embedded or secured adjacent shell 82 of capsule 10. This arrangement permits location of sensor 50 on a surface of capsule 10 to facilitate sensing biologic conditions. Capsule 10 optionally includes communication interface 66 to permit transmission and reception of data and signals relative to remote wireless communication system 20 (FIG. 1).

Figure 11:
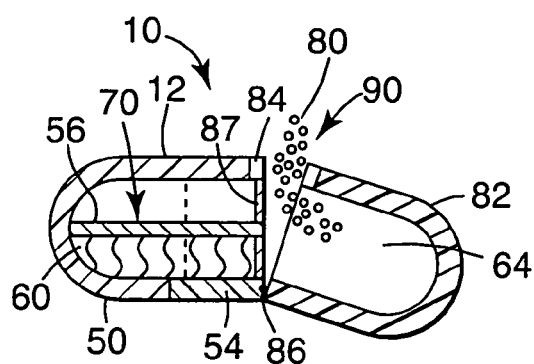
FIG. 11 is a sectional view of the internal drug dispenser capsule of FIG. 10 while the capsule dispenses a drug.

In addition, as shown in FIG. 10, capsule 10 comprises drug 80, first shell portion 82, second shell portion 83, fusible link 84, pivot 86, and barrier 87. Barrier 87 extends transversely across capsule 10 to contain drug 80 within drug storage module 64. Pivot 86 is disposed adjacent barrier 87 on one side of capsule shell 82 while fusible link 84 is disposed adjacent barrier 87 on an opposite side of capsule shell 82. Fusible link 84 is a releasable connecting member that maintains first shell portion 82 in sealed contact with second shell portion 83. Fusible link 84 is in electrical communication with controller 54 via an electrical pathway adjacent or within barrier 87. Fusible link 84 is selectively activated by an electrical signal from controller 54 to cause fusible link to release its connection between first shell portion 82 and second shell portion 83, thereby allowing second shell portion 83 to pivot open about hinge 86, as shown in FIG. 11. With capsule 10 opened, drug 80 is released from drug storage module 64 via passageway 90.

Figure 12:
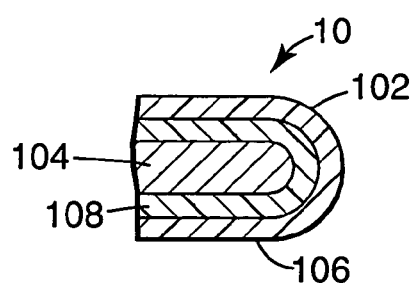
FIG. 12 is a partial sectional view of an alternative drug dispensing mechanism of the swallowable drug dispenser of FIG. 10.

FIG. 12 shows capsule 10 incorporating an alternative drug storage module 102. As shown, time release drug storage module 102 holds bioactive substance 104 within a pair of concentrically arranged outer shell 106 and inner shell 108. In this embodiment, at least one of inner shell 108 and outer shell 106 comprise a dissolvable coating while the remaining respective shell (106 or 108) comprises a shell that is selectively openable by the fusible link/pivoting mechanism of FIGS. 10–11, by reclosable ports, and/or other means known or devised by those skilled in the art. This arrangement permits one stage (either the first or second stage) of dispensing drug 80 to require mere exposure to the biologic environment while another stage (the respective first or second stage) of dispensing drug 80 require activation from controller 54 to the respective shell portion open to release drug 80. These dual shell mechanisms are suitable for carrying a biochemical substance past a harsh environment. For example, such arrangements can protect a fragile protein from an acidic low pH environment (e.g. stomach) while permitting release of the drug into a neutral or even slightly alkaline environment (intestine).

Figure 13:
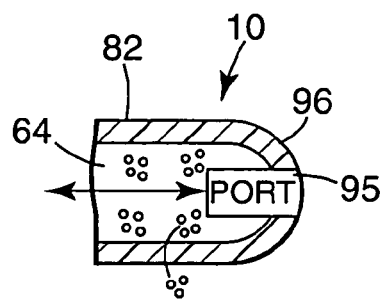
FIG. 13 is a partial sectional view of an alternative drug dispensing mechanism of the internal drug dispenser of FIG. 10

Other means of providing a selectively releasable drug supply can be used with capsule 10 of the present invention. For example, as shown in FIG. 13, drug storage module 64 optionally includes reclosable port 95 formed in a wall 96 of shell portion 82 to permit release of drug 80 at a predetermined variable controlled rate. Port 95 also permits initiation, termination of drug dispensing as well as acceleration and deceleration of the rate of dispensing through port 95. The reclosable shell portion or reclosable port 95 is used in association with sensors 50,52 and controller 54 to selectively permit release of drug 80 at a static or variable controlled rate in response to a sensed condition.

In use, capsule 10 operates internally within the digestive tract enabling dynamic "on-board" drug dispensing to the patient without active human or computer management and without remote wireless communication. Many different combinations of sensors, data profiles/criteria, and drug dispensing mechanisms of the present invention permit great flexibility in capsule design for a particular purpose. For example, sensing module 14, dispensing module 16, and memory component 18 can be used in the following types of procedures, among others.

In one example, sensor 50 of ingested capsule 10 senses a biologic condition (e.g. pH) within digestive tract 34. Using memory 56 and controller 54, data from sensor 50, 52 are compared to a profile and/or predetermined criteria stored in memory 56. Drug 80 is dispensed at a first static or variable controlled rate while a parameter is within a set range (e.g. 5 to 7 pH) and can be dispensed at a second static or variable controlled rate (or even discontinued) if the parameter falls out of the set range. The variable rate optionally includes accelerating rates and decelerating rates, as well as termination and/or repeated initiation of drug dispensing.

In another example, memory 56 stores a mapped profile of a sensed biologic condition (such as pH) as the data is sensed and holds a previously identified trigger level (e.g. pH above 7) as the predetermined criteria against which the sensed data is compared. Accordingly, once the senses data exceeds, matches, or is below the trigger level for a predetermine period of time, then drug 80 is dispensed from capsule 10.

A drug dispenser of the present invention carries many advantageous features. Foremost, the drug dispenser capsule selectively dispenses a drug within a digestive tract in response to a sensed biologic condition without communicating with a remote human or computer device located outside of the body. This feature permits the capsule to administer a drug to the patient without the cumbersome and inconvenient necessity to remain in close proximity to a remote signal transmitter/receiver, as is used in the prior art. Moreover, sensors in the capsule can sense data for recording in memory and/or sense data for comparison to data already stored in memory. The capsule 10 may also be implemented at a desired location within a body for long periods of time, sense and record data, and/or selectively provide drug therapy (i.e., dispense a drug), and can be removed at a later date for data retrieval and analysis.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the chemical, mechanical, electromechanical, electrical, and computer arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. A swallowable internal drug medical device comprising:
   a swallowable capsule including:
   a sensing module configured to sense a biologic condition within a digestive tract;
   a bioactive substance dispenser including a container for holding a volume of bioactive substance and a microactuator configured to dispense the bioactive substance from the container; and
   a memory and logic component in communication with the sensing module and the dispenser, including at least one of stored data of biologic conditions in the digestive tract and stored predetermined criteria for dispensing, the memory and logic component being configured to trigger the microactuator of the dispenser to dispense the bioactive substance when the sensed bodily condition corresponds to at least one of the stored data and the stored predetermined criteria.

2. The device of claim 1, wherein the capsule comprises a shell having a first portion and a second portion wherein the first portion is hingedly connected to the second portion and the second portion defines the bioactive substance container.

3. The device of claim 2, wherein the microactuator comprises a releasably fusible link disposed at a surface of the shell releasably securing the first portion to the second portion and being selectively actuable to selectively release the bioactive substance from the shell.

4. The device of claim 1, wherein the sensing module comprises at least one of a pH sensor, a temperature sensor, a glucose sensor, and a phenylalanine sensor.

5. The device of claim 1, wherein the memory and logic component comprises a programmable logic controller.

6. The device of claim 1, wherein the memory and logic component has a capacity of at least 10 megabytes.

7. The device of claim 1, wherein the memory and logic component has a power consumption of no more than 500 mW.

8. The device of claim 1, wherein the stored data of biologic conditions in the memory and logic component comprises a profile of predetermined values for a plurality of known biologic conditions.

9. The device of claim 1, further comprising:
   a remote ultrasonic transmission and receiver unit for location outside of a body; and
   an ultrasonic transmission and receiver unit disposed within the capsule and in communication with the remote unit;
   wherein the ultrasonic transmission and receiver unit is capable of transmitting sensed biologic data to the remote unit and the remote unit is capable of transmitting signals to the memory and logic component to trigger the microactuator of the bioactive substance dispenser, in cooperation with the memory and logic component, to dispense the bioactive substance from the container into the digestive tract.

10. The device of claim 1, further comprising a power supply connected to the memory and logic component.

11. The device of claim 1, wherein the sensing module comprises an array of sensors with each sensor detecting a different biologic condition.

12. The device of claim 1, wherein the sensing module comprises an array of sensors with each sensor detecting a different predetermined value of the same biologic condition.

13. The device of claim 1 wherein the microactuator is configured to initiate dispensing the bioactive substance without communication to a device external of the capsule.

14. The device of claim 1 wherein the microactuator is configured to initiate dispensing the bioactive substance independent of a device outside of the capsule.

15. The device of claim 1 wherein the sensed biologic condition corresponds to a known body location at which the bioactive substance is to be dispensed.

16. The device of claim 1 wherein the memory and logic component is configured to cause the microactuator to dispense the bioactive substance at a predetermined continuously variable rate in which the rate increases as a value of the sensed biologic condition increases and the predetermined continuously variable rate decreases as the value of the sensed biologic condition decreases.

17. The device of claim 1 wherein the memory and logic component is configured to cause the microactuator to dispense the bioactive substance at a predetermined continuously variable rate in which the rate decreases as a value of the sensed biologic condition increases and the predetermined continuously variable rate increases as the value of the sensed biologic condition decreases.

18. The device of claim 1 wherein the memory and logic component is configured to cause the microactuator to dispense the bioactive substance after a predetermined amount of time in the digestive tract and upon the sensed biologic condition sustaining a predetermined value for a predetermined amount of time.

19. A swallowable capsule comprising:
- means for sensing biologic conditions within a digestive tract;
- means for maintaining stored information about a plurality of bodily conditions within a digestive tract; and
- means for dispensing a drug from the capsule within the digestive tract, in communication with the means for sensing and the means for maintaining stored information, acting to dispense the drug based upon the biologic conditions sensed by the means for sensing and based upon the stored information in the means for maintaining stored information.

20. The swallowable capsule of claim 19, wherein the means for sensing comprises at least one of a pH sensor, a temperature sensor, a glucose sensor, and a phenylanine sensor.

21. The swallowable capsule of claim 19, wherein the means for sensing comprises an array of sensors with each sensor detecting a different biologic condition.

22. The swallowable capsule of claim 19, wherein the means for dispensing a drug acts to dispense the drug without communication to a device external of the capsule.

23. The swallowable capsule of claim 19, wherein the means for dispensing a drug acts to dispense the drug when the biologic conditions sensed by the means for sensing corresponds to a known body location at which the drug is to be dispensed.

24. The swallowable capsule of claim 23, wherein the means for dispensing comprises a container for holding a volume of the drug and a microactuator configured to dispense the drug from the container upon the sensed biologic conditions corresponding to the stored information.

25. The swallowable capsule of claim 24, wherein the container comprises a first portion and a second portion releasably secured to the first portion via a fusible link at a hinged connection between the first portion and the second portion and the microactuator is configured to cause dispensing of the drug from the container by actuating release of the fusible link to open the first portion relative to the second portion at the hinged connection.

* * * * *